Figure 1:
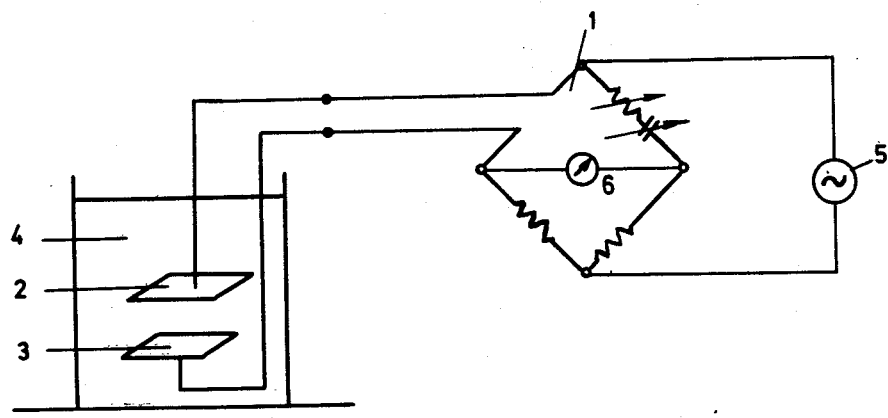

United States Patent [19]

Arwin et al.

[11] 4,072,576
[45] Feb. 7, 1978

[54] METHOD FOR STUDYING ENZYMATIC AND OTHER BIOCHEMICAL REACTIONS

[75] Inventors: Hans Rune Arwin, V. Frolunda; Kurt Ingemar Lundstrom, Goteborg, both of Sweden

[73] Assignee: AB Kabi, Stockholm, Sweden

[21] Appl. No.: 724,873

[22] Filed: Sept. 20, 1976

[30] Foreign Application Priority Data

Oct. 6, 1975    Sweden .................................. 7511148

[51] Int. Cl.² ........................ G01N 31/14; G01N 33/16
[52] U.S. Cl. ...................... 195/103.5 R; 195/103.5 A; 23/230 B; 204/1 T; 204/195 B
[58] Field of Search ............... 195/103.5 R, 103.5 M, 195/103.5 C, 103.5 A; 23/230 B; 204/1 T

[56] References Cited

U.S. PATENT DOCUMENTS

| | | | |
|---|---|---|---|
| 3,275,534 | 9/1966 | Cannon, Jr. et al. | 23/230 B |
| 3,479,255 | 11/1969 | Arthur | 195/103.5 R |
| 3,635,681 | 1/1972 | Rogers | 195/103.5 R |
| 3,884,896 | 5/1975 | Blomback et al. | 195/103.5 R |

*Primary Examiner*—Alvin E. Tanenholtz
*Attorney, Agent, or Firm*—Pollock, Vande Sande & Priddy

[57] ABSTRACT

Method for studying biochemical reactions in which a substance, whose activity or concentration is to be determined, affects a substrate specific for the biochemical reaction which includes providing electrodes coated with the substrate, determining as the control value, the capacitance in a measuring device containing the electrodes, introducing the substance into the measuring device, measuring the change in capacitance, and thereby obtaining a quantitative measure of the activity or concentration of the substance present in the sample and affecting the specific substrate on the electrodes.

16 Claims, 7 Drawing Figures

METHOD FOR STUDYING ENZYMATIC AND OTHER BIOCHEMICAL REACTIONS

The present invention relates to a method for studying enzymatic and other biochemical reactions of the type in which the substance, whose activity or concentration is intended for determination, affects a substrate specific for the biochemical reaction.

The method is among other things intended to be used for determination of enzymatic activity, especially for enzymes of the type serine proteases (thrombin, plasmin, trypsin etc). Several of these enzymes regulate the coagulation of blood and fibrinolysis and disorders in the normal enzyme quantities give reason to pathological changes such as heamorrhages or thrombosis.

The method can also be used for the study of immunologic reactions such as antigen-antibody couplings. Among other systems that also can be studied are inhibitor-enzyme couplings, receptor-hormone couplings and receptor-steroid couplings.

It is previously known to study enzymatic reactions by means of "enzyme electrodes" where the potential difference over membranes, specific for the waste products of the reaction, is measured. See also Gough D. A. and Andrade J. D., Enzyme Electrodes, Science Vol 180, pp 380–384.

When studying immunologic reactions it is known to use nickel metallized glass plates on which antigens have been adsorbed forming a layer on the surface, so that when the glass plate is immersed in a solution containing antibodies, there is a coupling between the antigens and the antibodies having the result that the thickness of the layer increases. The coupling is detected by measuring the thickness of the layer optically by means of an ellipsometer. See also Rothen A., Immunologic and enzymatic reactions carried out at a solid-liquid interface, Physiol Chem & Physics 5, 1973.

It is also previously known to determine enzymatic activity by means of a conductometrical method, see Lawrence A. J. and Moores G. R., Conductometry in Enzyme Studies, Eur J Biochem 24 (1972), pp 538–546.

It is also known that organic molecules may absorb on electrode surfaces and change the electrical properties of the electrodes, see Bockris J. O. M. and Reddy A. K. N., Modern Electrochemistry, Plenum Press, Vol 2, chap 7.

Also special substrates with high susceptibility to the enzymes in question have been developed, especially of the type amide substrate with the inherent ability to be hydrolyzed in the presence of the enzyme producing chromophoric products. The occurring change of colours may readily be measured spectrophotometrically, for instance by means of an optical absorption spectrometer. A substrate which is unable for optical detection of enzymatic activity and which facilitates clinical test of for instance the amounts of antithrombin and prothrombin is described in U.S. Pat. No. 3,884.896.

A disadvantage with the optical detection method is that a rather complicated and expensive apparatus is required and that a considerable amount of substrate is required in the measurement procedure. Furthermore, it is not possible to study the enzymatic activity directly in the blood because of the turbidity of blood. Instead of that it is necessary to work with plasma (the red blood cells removed) or serum (also the fibrinogen removed).

The purpose of the present invention is to provide a simple method in which mentioned disadvantages are eliminated. The invention is then mainly characterized in that at first the capacitance between two electrodes is measured in the presence of the substrate only and thereafter the capacitance is measured with the substance added, whose activity or concentration is intended for determination, whereby the change of capacitance per time unit or the total change in capacitance is a measure of the activity or concentration of the substance.

Figure 2:
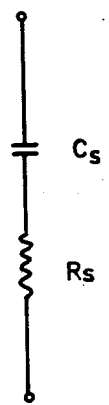
Figure 3:
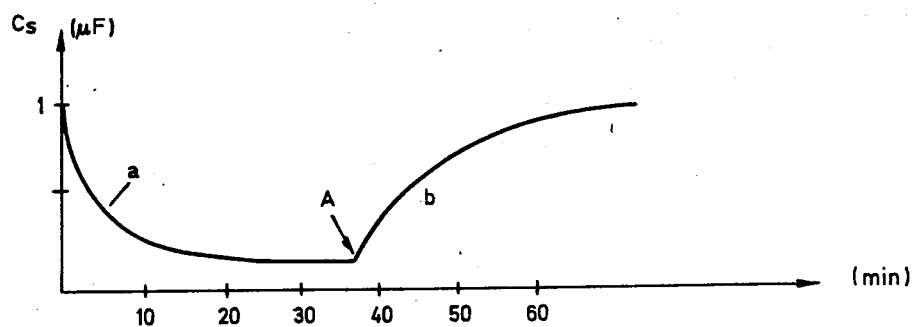
Figure 4:
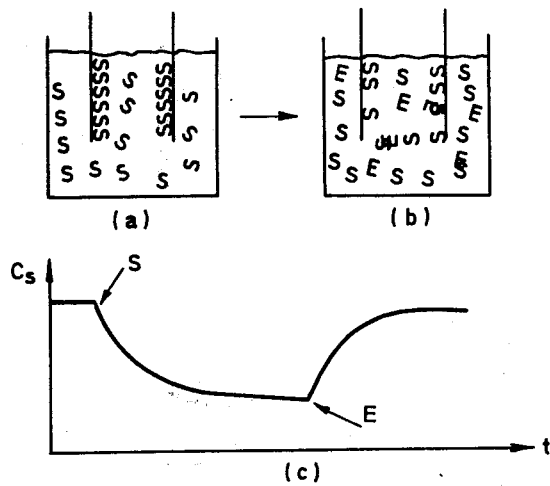
Figure 5:
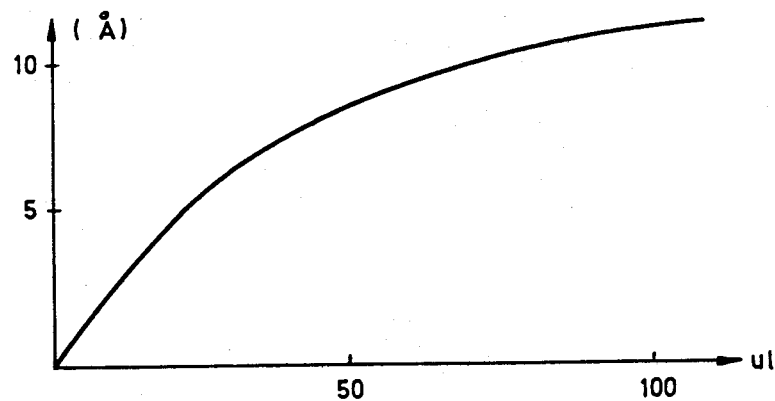
Figure 6:
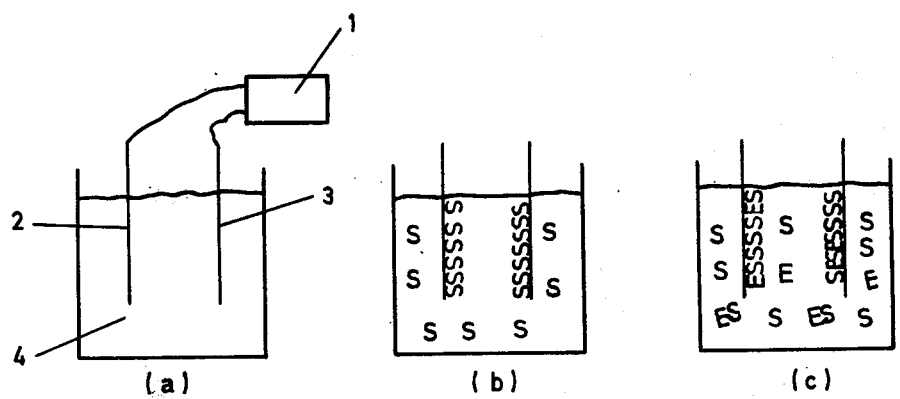
Figure 6:
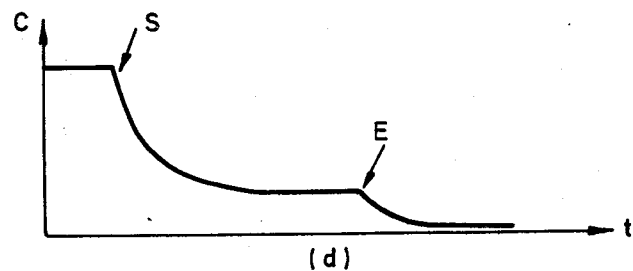
Figure 7:
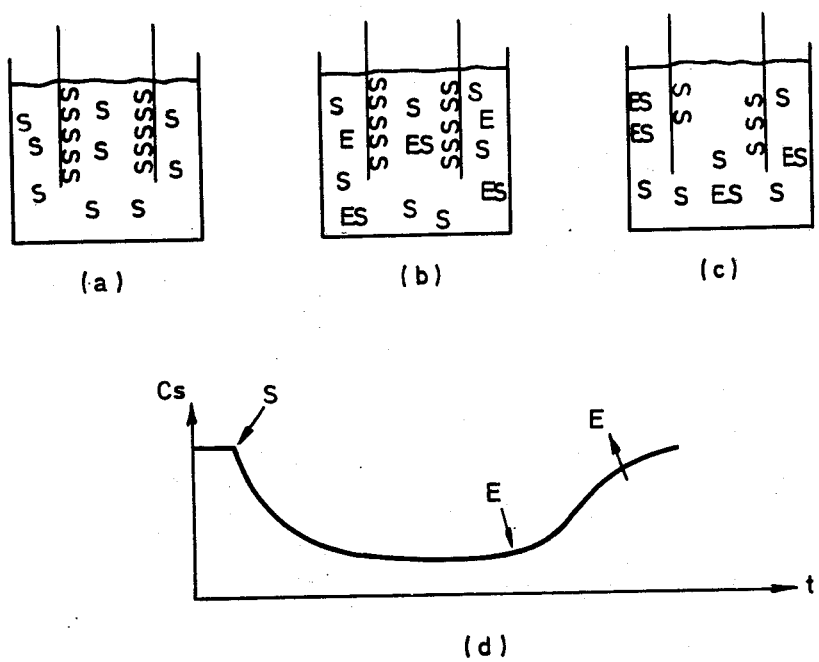

In the following the invention will be described more in detail with reference to the accompanying drawings in which FIG. 1 shows an electric measuring apparatus for measuring the capacitance between the electrodes, FIG. 2 shows a simplified equivalent circuit diagram of the measuring device, FIG. 3 shows a curve of the measured capacitance as a function of time, when substrate is added, FIG. 4 shows a schematic view of the procedure of determining enzymatic activity, FIG. 5 shows a curve of the coverage of adsorbed substrate molecules ($\sim 1/C_s$) as a function of the substrate concentration in the solution, FIG. 6 shows a schematic view of the procedure when studying an immunologic reaction, and FIG. 7 shows a schematic view of the procedure when studying a biochemical reaction in which the substrate in the surrounding solution is affected.

In the first exemplary embodiment the invention is described in connection with determination of enzymatic activity of serine proteases. The invention is based upon the fact that the substrate which is used has the inherent ability to absorb on a metallic surface and desorb in the presence of the enzymes in question. In FIG. 1 a measuring apparatus is shown by means of which the alternating voltage impedance between two platinum electrodes 2, 3 immersed in a solution 4 is measured. The measuring apparatus comprises an impedance bridge 1, a signal generator 5 and an amplifier with a zero detector 6. From the beginning the measuring device contains only a buffer solution with the pH = 8.2 and the ionic strength 0.15. At this pH value and ionic strength the investigated enzymes in question have optimal activity. As the ionic strength is high it gives rise to effects of electrode polarization if the measurement is evaluated at a relatively low frequency (100 kHz in this case). The series resistance $R_s$ is determined by the conductivity of the electrolyte and the capacitance $C_s$ mainly by the electrode polarization and a possible adsorbed layer of molecules.

According to FIG. 1 it is evident that the measuring device is connected in such a way that it constitutes one of the branches in the impedance bridge. If now a small amount of a polypeptide substrate of the kind mentioned in the U.S. Pat. No. 3,884,896 is added to the buffer solution, the measured capacitance $C_s$ varies as a function of time, see FIG. 3. The capacitance $C_s$ decreases as a function of time, see curve a in FIG. 3, depending on the fact that polypeptide molecules adsorb on the electrode surfaces. Gradually a balance is obtained between the polypeptide molecules in the solution and the molecules adsorbed on the electrode surfaces. A monomolecular layer of substrate molecules is then presumably adsorbed on the electrode surfaces.

If now an enzyme solution with the ability to split off the polypeptide is added at the point A in FIG. 3, then the measured capacitance $C_s$ will be changed again. The capacitance $C_s$ increases and returns to its original value, see curve b in FIG. 3. The change in the capacitance depends mainly on the fact that the added enzyme effects the adsorbed polypeptide. The added enzyme may be for instance thrombin, trypsin or plasmin (serine proteases), which hydrolyzes the polypeptide substrate whereby the adsorbed molecules completely or partly come loose or "is consumed", so that the capacitance of the measuring device is changed. The change in the capacitance per time unit, the initial slope of the curve b in FIG. 3, is a measure of the enzymatic activity.

The measuring device may be calibrated by means of a known amount of enzyme. The calibration curve may then be used when measuring on a solution with an unknown amount of enzyme. When measuring in blood plasma then the quantity of antienzyme is of interest. Mentioned quantity may be determined by adding a known amount of enzyme upon the blood plasma. After a few minutes, when the antienzyme is inhibited, the remaining amount of enzyme is measured. If this procedure is evaluated for two different enzyme or plasma quantities the original quantity of antienzyme can be extrapolated.

The procedure now described for determining enzymatic activity is schematically illustrated in FIG. 4, whereby FIG. 4a shows the measuring device with the electrodes immersed in the substrate solution, whereby the substrate molecules S are distributed among molecules in the solution and molecules absorbed on the electrode surfaces. At low concentration the ratio between them is kept constant. When the concentration increases, the electrode surfaces will gradually be filled and a smaller and smaller part of the added molecules will be adsorbed. In FIG. 5 a diagram illustrates the thickness of the layer at different concentrations of the polypeptide substrate (the quantity of polypeptide of the concentration 1 mM in 0.5 ml buffer solution). The diagram illustrates that presumably a monolayer of peptide molecules is adsorbed at high peptide concentrations. A further addition of the substrate then mainly increases the number of molecules in the solution.

If now an enzyme is added, see FIG. 4b, the enzyme molecules E will affect molcules in the solution as well as adsorbed molecules. In FIG. 4c it is illustrated how the series capacitance $C_s$ varies as a function of time when adding substrate molecules S and thereafter enzyme molecules E. As the measuring device only detects changes in the number of adsorbed molecules, it is desirable that as great a deal as possible affects the adsorbed molecules. An optimum in sensitivity is, therefore, expected in the presence of a certain amount of added peptide. At a low peptide concentration there is a loss in sensitivity because the electrode surfaces have a small filling efficiency and at high concentrations most of the added enzyme affects molecules in the solution. Measurements also indicate that such an optimum exists.

In the example just described the substrate consists of a polypeptide of the type described in the U.S. Pat. No. 3,884,896 with susceptibility to thrombin and other proteolytic enzymes of the type peptide peptidohydrolases. The substrate that has been used is hydrolyzed in the presence of the enzymes in question and produces a chromophoric product which may be measured spectrophotometrically. The substrate that has been used is by no means optimal for the electric detection which has been described, the main thing is that the substrate adheres thoroughly to the electrodes and that a significant part comes loose at the enzymatic hydrolysis which gives rise to a significant change in the capacitance of the metal electrodes. The substrate shall, therefore, adhere in such a way that the "sensitive" bond is accessible to the enzyme. Experiments have indicated that the substrate shall not entirely saturate the surface, for an optimum detection efficiency.

In the example which has been described the substrate has also been added to the buffer solution in the measuring device whereupon the substrate absorbes on the metal electrodes. One alternative is to provide the electrodes with a substrate layer before the measurement, i.e. to use pre-prepared electrodes and study the resulting change in capacitance when these electrodes are dipped into the enzyme solution in question. Consequently, it is not necessary that the substrate adsorbes on the metal electrode, the substrate may for instance be chemically bound to the electrode surface provided that the substrate molecules have such properties that the "sensitive" bond is accessible to the enzyme and that a part of or the entire substrate molecule comes loose, when the enzyme affects the molecule.

FIG. 6 shows an example in which the measuring device is used for studying an immunologic reaction of the type antigen-antibody binding. In conformity with the example just described the capacitance between two electrodes 2, 3 is measured by means of an impedance bridge 1 with the same constructonal feature as that of FIG. 1. The electrode surfaces are either prepared with antigens from the beginning or the electrodes have been immersed in a solution with antigens whereby antigens adsorb on the electrode surfaces and the capacitance is measured for this case. Then the electrodes are immersed in the solution containing antibodies whereby the antibodies are bound to the adsorbed antigens, so that the layer on the electrode surfaces increases, i.e. the capacitance $C_s$ decreases. FIG. 6a illustrates the electrodes immersed in a buffer solution 4 and when adding antigen molecules (indicated with S) there is an adsorption on the electrode surfaces of antigen molecules, until at last balance is kept between antigens in the solution and antigens adsorbed on the electrode surface, see FIG. 6b. In FIG. 6c finally the procedure of adding antibodies E to the solution is illustrated. Some of the antibodies are bound to antigens in the solution and some of them to antigens on the electrode surface. Even here there is balance at last, see the curve 6d, which illustrates the series capacitance $C_s$ between the electrode surfaces as a function of time when adding antigens (S) and antibodies (E). The initial slope of the curve after the addition of the antibodies (E) is determined by the concentration of antibodies, which gives a quantitative measure of it. A quantitative measure of the concentration of antibodies may also be evaluated from the entire capacitance change when adding antibodies.

In the example now described the specific substrate consists of antigens whose molecules must have the ability to adhere to the electrodes in such a way that the molecules of the antibodies are able to be bound to the antigen molecules and further that the antigen-antibody layer which is formed shall be kept strong enough on the electrode. If the antigen-antibody complex comes loose from the electrode surface then this method works according to the previous example.

Even for antibody detection there is an optimal concentration of antigens depending on the balance occurring between antigens in the solution and antigens on the electrode surface and even a balance between single and bound antigen and antibody molecules, respectively.

In case that the substance which is studied affects only the substrate in the solution the method if carried out in the following way.

When a substance is added to the solution in the measuring device which substance affects only the substrate in the solution then the concentration of substrate molecules will decrease. In order to maintain the balance between substrate in the solution and substrate adsorbed the adsorbed substrate will come loose from the electrode surface resulting in a decrease of the layer on the electrode surface and an increase in the capacitance $C_s$, see FIG. 7d. The capacitance change per time unit, the slope of the curve when the substance which gives a quantitative measure on this. The same thing applies for the total capacitance change (after a long time), which consequently can be used as a measure of the concentration or activity of the substance in question.

In many cases the added substance affects both the substrate in solution and the substrate on the electrode. The capacitance change then depends on two processes but is still a quantitative measure of the concentration or activity of the added substance.

In the examples which have been described platinum electrodes were used. As electrode material even other metals may be used. Metals as copper, silver, molybdenum, titanium, gold, palladium and nickel chrome have been proved to work as well as electrode material. It is realized, however, that even other types of electrodes, like semiconductor electrodes may be used. For the examples it further holds that the impedance bridge preferably is provided with outputs displaying the capacitance change per time unit ("instant enzyme activity") and total capacitance change ("integrated enzyme activity") for the sample in question.

This invention is not limited to said examplary methods but various modifications may be made without departing from the spirit and scope of the invention.

We claim:

1. Method for determining the activity of concentration in a sample, of a biochemical substance which biochemically affects a substrate that is specific for the biochemical substance which comprises:
   providing metallic or semiconductor electrodes coated with said substrate,
   determining as a control value, the capacitance in a measuring device of said metallic electrodes or semiconductor electrodes coated with said substrate,
   introducing the sample to be tested for the determination of the activity or concentration of said substance into said measuring device so as to contact said coated electrodes with said sample,
   measuring the change in capacitance due to a change in the amount of biochemically uneffected substrate coated on said electrodes, and thereby obtaining a quantitative measure of the activity or concentration of said substance, present in the sample and affecting the specific substrate on the electrodes.

2. The method of claim 1 wherein the coated electrodes are prepared by immersing the metallic or semiconductor electrodes in a solution containing a substrate which is capable of adsorbing on the surfaces of said electrodes.

3. The method of claim 2 wherein the molecules of said substrate adsorbed on the electrode surfaces completely or partially dissociate and thereby are desorbed upon introducing said substance.

4. The method of claim 2 wherein the molecules of said substrate adsorbed on the electrode surface bind molecules of said substance thereby increasing the layer thickness of the electrode surfaces upon introducing said substance.

5. The method of claim 1 which comprises measuring the capacitance between the electrodes by using an electric impedance bridge.

6. The method of claim 1 wherein said substance whose activity or concentration is to be determined are serine proteases, and said substrate is synthetic splittable polypeptide specific for serine proteases.

7. The method of claim 6 wherein said substrate is represented by the formula:

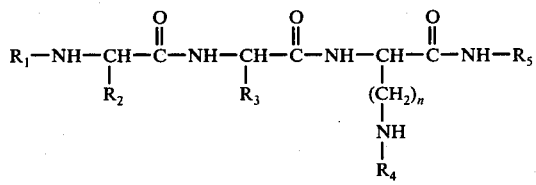

or salts thereof, where $R_1$ is hydrogen, an alkyl-carbonyl having 1-12 carbon atoms, a $\omega$-aminoalkyl-carbonyl having 1-12 carbon atoms in a straight chain, cyclohexyl-carbonyl, a $\omega$-cyclohexylalkyl-carbonyl having 1-6 carbon atoms in a straight chain, 4-amino ethyl-cyclohexyl-carbonyl, benzoyl, benzoyl substituted with one or more substituents selected from halogen atoms, methyl, amino and phenyl groups, a $\omega$-phenyl-alkylcarbonyl having 1-6 carbon atoms in a straight chain, benzenesulphonyl, 4-toluene-sulphonyl or N$\alpha$-benzoyl-phenylalanyl; $R_2$ is phenyl, benzyl, 4-hydroxy-benzyl, 4-methoxybenzyl or 4-methylbenzyl; $R_3$ is a straight, branched or cyclic alkyl having 3-8 carbon atoms, phenyl, or benzyl; $n$ is 3 or 4; $R_4$ is hydrogen or quanyl; and $R_5$ is phenyl, nitrophenyl, methylnitrophenyl, dinitrophenyl, naphthyl, nitronaphthyl, quinolyl or nitroquinolyl.

8. The method of claim 4 wherein the molecules of said substrate are inhibitors to the molecules of said substance.

9. The method of claim 4 wherein the molecules of said substrate are receptors for hormones whose activity or concentration is to be determined.

10. The method of claim 1 wherein said biochemical substances are enzymes.

11. The method of claim 1 wherein said electrodes are metallic electrodes.

12. The method of claim 11 wherein said electrodes are selected from the group consisting of platinum, copper, silver, molybdenum, titanium, gold, palladium, and nickel chrome.

13. The method of claim 11 wherein said electrodes are platinum electrodes.

14. The method of claim 11 wherein said electrodes are coated with a monomolecular layer of said substrate.

15. The method of claim 1 wherein said substrate is chemically bound to said electrode.

16. The method of claim 1 wherein said surfaces of the electrodes are not entirely saturated with said substrate.

* * * * *

UNITED STATES PATENT AND TRADEMARK OFFICE
CERTIFICATE OF CORRECTION

PATENT NO. : 4,072,576
DATED : February 7, 1978
INVENTOR(S) : Hans Rune Arwin et al It is certified that error appears in the above-identified patent and that said Letters Patent are hereby corrected as shown below:

In Claim 1, lines 1 and 2, change "activity of concentration" to -- activity or concentration ---.

Signed and Sealed this

Twenty-second Day of August 1978

[SEAL]

Attest:

RUTH C. MASON
Attesting Officer

DONALD W. BANNER
Commissioner of Patents and Trademarks